United States Patent [19]

Ross

[11] Patent Number: 5,093,182

[45] Date of Patent: Mar. 3, 1992

[54] SUSTAINED-RELEASE, PRINT-COMPATIBLE COATINGS FOR FRAGRANCE SAMPLERS

[75] Inventor: Jamie S. Ross, Chattanooga, Tenn.

[73] Assignee: Arcade, Inc., Chattanooga, Tenn.

[21] Appl. No.: 583,496

[22] Filed: Sep. 17, 1990

[51] Int. Cl.$^5$ .............................. B32B 9/00
[52] U.S. Cl. ................. 428/195; 428/537.5; 428/905; 427/258
[58] Field of Search .............. 428/195, 537.5, 905; 427/258

[56] References Cited

U.S. PATENT DOCUMENTS

| | | | |
|---|---|---|---|
| 4,631,231 | 12/1986 | Stendel et al. | 428/905 |
| 4,769,264 | 9/1988 | Dreger | 428/905 |
| 4,908,252 | 3/1990 | Carnahan et al. | 428/905 |
| 4,925,517 | 5/1990 | Charbonneau et al. | 428/905 |

FOREIGN PATENT DOCUMENTS

| | | |
|---|---|---|
| 2116864 | 10/1972 | Fed. Rep. of Germany . |
| 54-70373 | 6/1979 | Japan . |
| 1444981 | 8/1976 | United Kingdom . |

*Primary Examiner*—Patrick J. Ryan
*Attorney, Agent, or Firm*—Phillips & Beumer

[57] ABSTRACT

A sustained-release, perfume-containing coating is provided for applications to advertising samplers and the like. A coating is made up of perfume oil having dissolved therein a suitable polymer, and particularly ethyl cellulose, in an amount sufficient to provide a specified viscosity that enables ready application to a substrate by printing and prevents interaction of fragrance oil with a printed image. Advertising samplers having such a coating applied to a paper substrate are also disclosed. The samplers may have a printed image applied thereto underneath the perfume-containing coating. The polymer in the perfume oil serves to modify the oil so as to cause the fragrances therein to be released slowly and without premature release of top-note components. This measure also prevents degradation of the perfume oil from inks used to print images on the sampler.

19 Claims, No Drawings

SUSTAINED-RELEASE, PRINT-COMPATIBLE COATINGS FOR FRAGRANCE SAMPLERS

FIELD OF THE INVENTION

This invention relates to sustained-release, perfume-containing coatings and to sampler products using such coatings.

BACKGROUND OF THE INVENTION

Various approaches have been used for introducing the general public to perfume fragrances, one of the oldest being direct application by spraying a small sample onto the wrist or arm at a store counter. This approach has a limited appeal owing to the reluctance of a large segment of the public to have a fragrance with which they are not familiar applied directly to their person. This reluctance may be motivated by a fear of an adverse or allergic reaction, a concern that the sprayed fragrance will interfere with a previously applied fragrance, or that the sprayed fragrance will be too strong. Spraying of a fragrance on a model card or tissue and allowing the customers to take the card with them is another method which has been used. A serious problem with this method of advertising is that the customer may try several fragrances at once and place them in a bag, where they tend to blend, causing a confusing and negative experience. Also, the sprayed-on perfume after a relatively short period of time loses its volatile top notes and even some middle notes, resulting in an aroma that is substantially different from when first sampled.

Controlled release of fragrance from a sampler is the way to avoid the problems described for sprayed-on sampling. One example of controlled release technology is the pull-apart sampler. In the pull-apart sampler, the fragrance is microencapsulated, and the fragrance microcapsules are safely protected under a paper fold until such time as the sampler is opened. Opening the sampler breaks the microcapsules and liberates most of the fragrance at once. Until the microcapsule walls are ruptured, the fragrance is held in place, unchanged. After opening the sampler, the fragrance can be applied to the skin, if the recipient so desires, by rubbing the microcapsules upon the skin. The rubbing usually breaks more capsules, freshening and strengthening the fragrance. Pull-apart samplers are manufactured by mass production methods, often in a large printing plant. Such samplers with high quality printing are used as magazine inserts and direct mailings that reach large numbers of people, many of whom may not have the opportunity to sample fragrances while shopping. The general public receives these samplers at home where they can be opened at their leisure and in environments generally free from competing aromas. A disadvantage associated with this approach is that soon after opening the sampler, the fragrance disappears.

It is desired to provide perfume samplers in the form of printed cards or sheets of paper or other material that have a perfume-containing, sustained-release coating applied to a surface thereof. This would allow the fragrances to be dispensed over a prolonged period without loss of accuracy of the perfume blend due to the rapid escape of more volatile components that occurs when release of the perfume is not restrained. In addition to providing for sustained release, the perfume-containing coatings for such samplers should be compatible with printed matter that would preferably be included on the sampler in the same area as the coating. Previous attempts to provide a perfume-containing image on cards or the like have been characterized by problems due to an interaction of the perfume oil and ink on the printed matter. This interaction tends to contaminate the perfume, destroying its effectiveness, as well as to distort or remove portions of the printed matter.

Prior patents disclose several types of polymeric systems and compositions which include components for providing a sustained-release effect to perfume contained therein. British Patent No. 1,176,262, published Jan. 1, 1970, discloses a perfume carrier material, to be applied to sheet material by printing, that includes a wax such as Ozokerite and a lubricant such as petroleum jelly, along with a varnish and a small amount of perfume. Inclusion of a wax as required in this patent may result in degradation of the perfume fragrance inasmuch as the wax imparts a fragrance of its own that becomes mixed with the perfume fragrances. U.S. Pat. No. 3,985,298, issued Oct. 12, 1976, to Nichols, discloses controlled-release materials and methods wherein active ingredients to be released are incorporated in a "polymer-liquid composite" material as sparingly soluble particles or a precipitate. The disclosed method requires the use of a liquid phase which may be water or alcohol as well as a polymer liquid phase and particulate materials, resulting in process complexity. U.S. Pat. No. 4,528,125, issued July 9, 1985, to Alderman et al., discloses sustained release compositions comprising an aqueous dispersion of a water-insoluble cellulose ether that has an active agent reversibly diffused therein. Aqueous dispersions containing fragrance oil prepared in the manner disclosed in this patent are not compatible with printed matter, the fragrance oil interacting with and becoming degraded by printing ink. U.S. Pat. No. 4,720,409, issued Jan. 19, 1988, to Spector, discloses a transparent fragrance-emitting film having a polymeric matrix impregnated with a volatile fragrance, this film being backed by other films that include artwork. No disclosure is given regarding how the fragrance-containing film is produced. U.S. Pat. No. 2,169,055, issued Aug. 8, 1939, to Obershiner, discloses a perfume fixitive wherein a scent-imparting essential oil is added to a solution of cellulose acetate in an organic solvent, and a diethyl phthalate plasticizer is provided. The solvent is then removed to form a film or sheet. U.S. Pat. No. 4,617,147, issued Oct. 14, 1986, to Shibanai, discloses the preparation of a gel-like solid perfume with a persistent fragrance obtained by adding a perfume oil to an alcohol solution of hydroxypropyl cellulose with a solution of dibenzylidenesorbitol in N-methyl-2-pyrrolidone to inactivate the perfume oil. U.S. Pat. No. 3,565,831, issued Feb. 23, 1971, to Lubbecke, discloses a sprayable fragrance composition made up of a fragrance oil, a cellulose ether fixative, a volatile organic solvent, and a rosin ingredient. While these patents disclose fragrance compositions that include cellulose compounds to obtain sustained release of fragrance, they are not concerned with providing compatibility of the perfume-containing composition with printed images where both are applied to the same article during the printing process.

SUMMARY OF THE INVENTION

The present invention is directed to a sustained-release perfume-containing coating obtained from a non-aqueous solution or dispersion of a selected polymeric material such as ethyl cellulose in perfume oil for application to a substrate of an advertising sampler or the like in combination with an ink-printed image applied to the same article. Properties necessary for effective application of the coating, in particular, viscosity and tack, may be provided by adjustment of the relative proportion of perfume oil and polymer. Coatings embodying the invention may be readily applied to a variety of substrates and in particular to paper sheets or cards suitable for use as advertising samplers. The coatings may be applied by various means, and they are suitable for being supplied on a large scale process by conventional printing equipment. These coatings show a high degree of compatibility with printed matter located on the same area of a sample to which they are applied, the perfume oil being tied up in a polymer matrix to an extent such that it does not react with ink in the printed matter, and interference of the ink with the perfume fragrance or degradation of a printed image by the perfume oil is avoided. Premature loss of more volatile, top-note components of the fragrance, which would result in a degraded rendition of the fragrance blend, is prevented; and the possibility of adulteration of the fragrance by reaction with other components such as waxes, solvents, plasticizers, or an aqueous phase that have been used in prior coated compositions may be avoided in this invention by including only the polymer and perfume oil. We have found that such additives are not necessary to obtain a readily applied, effective coating. Other components may be included only if they are found to be non-adulterative.

It is, therefore, an object of this invention to provide a sustained-release, perfume-containing coating that avoids excessive release of top-note fragrance components.

Another object is to provide a sustained-release, perfume-containing coating that may be applied to paper or other substrates having printed images thereon without producing a reaction between perfume oils and the ink present in such images.

Yet another object is to provide a method of preparing such a coating wherein use of an aqueous phase is avoided.

Still another object is to provide an advertising sampler having printed thereon an ink image and a sustained-release, perfume-containing composition that is compatible with the printed ink image.

Other objects and advantages of the invention will be apparent from the following detailed description.

DESCRIPTION OF THE PREFERRED EMBODIMENT

A perfume-containing composition to be applied as a coating for an advertising sampler or the like having an image imprinted thereon may be prepared by dissolving a selected polymer and preferably ethyl cellulose in a fragrance oil in the absence of any aqueous phase, with the amount and properties of the polymer being controlled to produce a required viscosity and tackiness to facilitate its application as a coating. The perfume oil may comprise natural or synthetic essential oils which include a variety of fragrance components differing from one another in their chemical functionality, molecular weight, and volatility. Such oils are available in the form of specific blends that provide a desired aroma. Fixatives such as isopropyl myristate, DEP (diethylphthalate), methylglucose ether, benzyl benzoate, or BHT (butylated hydroxytoluene) may also be included in such oils up to a proportion of 50 weight percent. The perfume oils to which the present invention applies are primarily those designated in the art as "fine" perfumes, although other fragrances or fragrance-emitting flavors may also be used. The coating may also incorporate fragrances that serve as repellents, attractants, deodorants, or pharmaceutically beneficial odors such as menthol.

The preferred polymer, ethyl cellulose, may be provided in a form having a solution viscosity of six to eight centipose as measured in accordance with the manufacturer's specifications, in a ubbelohde viscometer at 25° C. This material is available from Dow Chemical Company under the designation Ethocel-7 TM. For this form of ethyl cellulose, required properties of the coated composition are obtained by using 5 to 50 weight percent and preferably 25 weight percent ethyl cellulose, and the balance perfume oil. When dissolved or dispersed in perfume oil, this produces a coating material having a viscosity of 7,500 to 300,000 cps, and 110,000 cps at the preferred amount. Other forms of ethyl cellulose having a different starting viscosity such as Ethocel-4 and Ethocel-10 may also be used, with the amount being adjusted to provide a viscosity in the composition that is as stated above. In addition, other polymers such as cellulose acetate propionate, cellulose acetate butyrate, ethyl hydroxy cellulose, or ethyl hydroxyethyl cellulose may be used in an amount such as to provide the necessary viscosity and tack.

The resulting viscous solution having the preferred viscosity and content of components is particularly adapted to being applied to substrates of paper and other sheet material by printing, using conventional equipment such as an offset printing press. The viscous solution resembles overcoat varnish in its physical characteristics, thus allowing it to be applied by printing in the same manner as inks. Upon being applied by printing, the coating rapidly dries without being heated, forming a clear, non-opaque layer having the perfume tied up to an extent such as to provide for sustained release for an extended period, without being degraded by loss of top-notes. Other methods of application such as rod coating, extrusion, spraying, brushing, or curtain coating may also be used.

In a preferred embodiment for an advertising sampler, the coating as described above is applied to an uncoated paper sheet or card, although the paper may be coated on one side or both. Printed images may be included in a sampler product, with the image being applied by conventional printing prior to applying the perfume-containing coating. Unlike prior perfume-containing coatings, the present coating may be applied over the same area or on top of the printed image without distortion of the image or the rendition of the perfume. The perfume-containing coating is generally clear and non-opaque and thus does not significantly interfere with the printed image.

The invention is illustrated by the following examples.

EXAMPLE 1

Five pounds of a fragrance essential oil was placed in a one-gallon container under agitation with a laboratory motor and stirring blade. One and a half pounds of Ethylcellulose STD 7 (Dow) was sifted into the fragrance essential oil and mixed until dissolved.

This composition was then placed in the ink fountain of a sheet-fed, four-color printing press, and the press was run as during a normal printing operation except that the fragrant composition was substituted for printing ink. Thirty-five-inch sheets of coated one-side paper, with advertising printed on the coated side, were then run through the press so that the composition was applied to the uncoated side of the sheet.

The composition dried to the touch rapidly so that there is no offsetting or smearing caused by the composition in contact with any printed articles, and the sheets were cut down to the size of the advertisement printed on the coated side. These advertisement cards released a powerful scent and were packaged in packs of 50 and 100. After prolonged storage, the cards, when removed from the package, released a scent powerful enough to scent a large room.

EXAMPLE 2

The procedure of Example 1 is repeated except that two pounds of Ethylcellulose is added to the essential oil and, once dissolved, the composition is diluted 20 percent with DEP (Diethylphthalate). This composition was run through a two-color, sheet-fed press similar to Example 1. The advertisements produced had an extremely powerful scent when dry to the touch.

EXAMPLE 3

The procedure of Example 1 is repeated except that after the Ethylcellulose is dissolved, the composition is diluted 30 percent with SD40B ethanol, and the composition is run from the ink fountain of a web press and applied to the coated side of a continuously moving web of paper. This composition is extremely quick to dry, and the web may be sheeted or rewound during the finishing process. Advertisement samples produced in this manner exhibited a strong and effusive odor.

EXAMPLE 4

The procedure of Example 3 is followed, with the sole exception that the composition is applied to a web of glassine or cellulose acetate. After drying, this article likewise possesses substantially the same characteristics indicated above for the article in Example 3.

EXAMPLE 5

The procedure of Example 3 is followed, with the sole exception that the composition is applied to a web of Teslin, a biaxially oriented polypropylene plastic material designed to run through a printing operation and produced by PPG Industries, Inc.

After drying rapidly, this article likewise possesses substantially the same characteristics indicated above for the articles in Examples 3 and 4.

EXAMPLE 6

The procedure of Example 1 is followed, with the sole exception that the fragrant composition is run from each of four ink fountains, thus producing four contiguous layers of the composition down upon the sheet. After drying, this article likewise possesses substantially the same characteristics as indicated in the previous examples, except that it is even longer lasting. After prolonged storage, samples continue to release a powerful odor, filling a whole large room from one small 3"×5" card.

EXAMPLE 7

The procedure of Example 1 is repeated except that the essential oil utilized is a lemon flavor, and the stock used is a 100# uncoated blotter. This article dries immediately and releases a powerful lemon scent for an extended period.

EXAMPLE 8

The procedure of Example 1 is repeated except that the sheet-fed press utilized is a lab top AB Dick, Model 321 Offset Duplicator, and the press sheets used are 8½"×11". The fragrance used in this composition was gardenia and, when dried, released a powerful lasting odor essentially similar to the above-mentioned examples.

EXAMPLE 9

One hundred twenty grams of a fragrance essential oil was placed in a lab beaker and put under agitation. Thirty-six grams of Ethylcellulose STD 7 was sifted into the fragrance essential oil and stirred until dissolved. This composition was diluted 10 percent with IPM (Isopropyl myristate) and 40 percent with SD40B ethanol.

The composition was then applied to 8½"×5½" sheets of coated, one-side paper on the uncoated side by hand draw down with a #4 Meyer rod. Two passes were performed, and the article dried rapidly to release a long-lasting and powerful, effusive scent.

EXAMPLE 10

The procedure of Example 9 is followed, with the sole exception that Ethylcellulose STD 10 (Dow) is used. The articles produced exhibit substantially the same characteristics indicated above for the articles in Example 9.

The above examples are merely illustrative and are not to be understood as limiting the scope of the invention, which is limited only as indicated by the following claims.

I claim:

1. A fragrance-releasing, image-displaying article comprising a substrate having deposited thereon a printed image and a fragrance-containing coating composition comprising an unencapsule fragrance oil having dissolved or dispersed therein a sustained-release agent selected from the group consisting of ethyl cellulose, cellulose acetate propionate, and ethyl hydroxy ethyl cellulose in an amount effective to prevent interaction of said fragrance oil with said printed image.

2. An article as defined in claim 1 wherein said sustained release agent is ethyl cellulose.

3. An article as defined in claim 2 wherein said substrate is a paper sheet of an advertising sampler, and said image is advertising material.

4. An article as defined in claim 3 wherein said paper sheet is coated on at least one side.

5. An article as defined in claim 4 wherein said sheet is coated on one side, the printed image is applied to the coated side, and the fragrance-releasing coating is applied to the uncoated side.

6. An article as defined in claim 2 wherein said ethyl cellulose is provided in said coating composition at a proportion of 5 to 40 weight percent thereof.

7. An advertising sampler comprising:
 a paper sheet;
 an ink image printed on said sheet;
 a sustained-release, fragrance-containing coating composition printed on said sheet; and
 said coating composition comprising a continuous phase of fragrance oil having dissolved or dispersed therein ethyl cellulose in an amount effective to prevent interaction of said fragrance oil and said printed image.

8. A sampler as defined in claim 7 wherein said paper sheet has a coated side and an uncoated side, said image is printed on said coated side, and said coating composition is printed on said uncoated side.

9. A sampler as defined in claim 7 wherein said coating composition is printed over said image.

10. An article as defined in claim 1 wherein said coating composition is a non-aqueous solution or dispersion.

11. An article as defined in claim 1 wherein said fragrance oil in said coating composition is in the form of a continuous phase.

12. The method of preparing a fragrance-releasing, image-displaying article which comprises:
   providing a substrate;
   printing an ink image onto said substrate; and
   applying to the printed substrate a coating composition comprising an unencapsulated fragrance oil having dissolved or dispersed therein a sustained-release agent selected from the group consisting of ethyl cellulose, cellulose acetate proprionate, and ethyl hydroxy ethyl cellulose in an amount effective to prevent interaction of said fragrance oil with said printed image.

13. A method as defined in claim 12 wherein said sustained-release agent is ethyl cellulose.

14. A method as defined in claim 13 wherein said substrate is a paper sheet of an advertising sampler.

15. A method as defined in claim 14 wherein said paper sheet is coated on at least one side.

16. A method as defined in claim 15 wherein said sheet is coated on one side, the printed image is applied to the coated side, and the fragrance-releasing coating is applied to the uncoated side.

17. A method as defined in claim 12 wherein said coating is applied by printing.

18. A method as defined in claim 13 wherein said substrate is biaxially oriented polypropylene.

19. The method as defined in claim 12 including the step of preparing said coating composition in the absence of an aqueous phase.

* * * * *